United States Patent [19]

Giddings

[11] Patent Number: 4,894,146
[45] Date of Patent: Jan. 16, 1990

[54] THIN CHANNEL SPLIT FLOW PROCESS AND APPARATUS FOR PARTICLE FRACTIONATION

[75] Inventor: John C. Giddings, Salt Lake City, Utah

[73] Assignee: University of Utah, Salt Lake City, Utah

[21] Appl. No.: 196,449

[22] Filed: May 20, 1988

Related U.S. Application Data

[63] Continuation-in-part of Ser. No. 67,487, Jun. 29, 1987, abandoned, which is a continuation-in-part of Ser. No. 822,529, Jan. 27, 1986, abandoned.

[51] Int. Cl.$^4$ ............................ B03B 7/00; B03C 5/00
[52] U.S. Cl. ........................................ 209/12; 209/40; 209/127.1; 209/129; 209/131; 209/210; 209/478; 209/493; 210/748
[58] Field of Search ...................... 209/1, 2, 12, 18, 39, 209/40, 127.1, 129, 131, 132, 156, 155, 173, 208, 210, 422, 478, 493, 532.1; 210/222, 223, 243, 695, 748, 321.63, 321.65, 321.75

[56] References Cited

U.S. PATENT DOCUMENTS

| | | | |
|---|---|---|---|
| Re. 31,688 | 9/1984 | Popovich et al. | 210/321.65 |
| 3,140,714 | 7/1964 | Murphy | 209/2 |
| 3,212,498 | 10/1965 | McKirdy | 210/321.75 |
| 4,250,026 | 2/1981 | Giddings | 209/156 |
| 4,284,498 | 8/1981 | Grant | 209/155 |
| 4,487,689 | 12/1984 | Galaj | 210/321.63 |
| 4,657,676 | 4/1987 | Keary | 209/155 |
| 4,737,268 | 4/1988 | Giddings | 209/12 |

Primary Examiner—Andres Kashnikow

[57] ABSTRACT

A thin channel split flow process for particle fractionation which effects a rapid and efficient separation of the particles comprising continuously introducing two or more fluid substreams of different composition into separate inlet ports of a thin enclosed channel having a thickness which is very thin compared to the other two dimensions and bringing the substreams into contact with adjacent substreams so as to collectively form a series of thin laminae flowing parallel to one another in the channel and in contact with one another over a sufficient length of channel to allow a desired level of mass transport between and through laminae, continuously introducing a fluid medium containing the particles to be separated as one or more of the fluid substreams and independently of the particle concentration, varying the fluid composition of the different substreams as needed to realize separation, at the outlet end of the channel splitting the collective streams into another set of substreams so as to permit separate recovery of one or more of the substreams.

32 Claims, 2 Drawing Sheets

THIN CHANNEL SPLIT FLOW PROCESS AND APPARATUS FOR PARTICLE FRACTIONATION

This application is a continuation-in-part of my application Ser. No. 067,487, filed Jun. 29, 1987, now abandoned, which is a continuation-in-part of my parent application Ser. No. 822,529, filed Jan. 27, 1986, also abandoned.

BACKGROUND OF THE INVENTION

1. Field of the Invention

This invention relates to a new process for particle fractionation. More particularly, the invention relates to a new process for the separation of particles or molecules according to size or to other physical characteristics, and to a new type of apparatus for accomplishing the same.

Specifically, the invention provides a new continuous process for separation of particles which gives a surprising and unexpected increase in the resolution and speed of separation compared to known methods. The new process broadly comprises continuously introducing two or more fluid substreams of different composition into separate inlet ports of a thin enclosed channel having an inlet and outlet end and having a thickness which is very thin compared to the other two dimensions and bringing the substreams into contact with adjacent substreams so as to collectively form a series of thin laminae flowing parallel to one another within the channel and in contact with one another over a sufficient length of channel to allow a desired level of mass transport between and through laminae without substantial hydrodynamic mixing between the laminae, continuously introducing a fluid medium containing the particles to be separated as one or more of the fluid substreams and independently of the particle concentration, varying the fluid composition of the different substreams as needed to realize separation, at the outlet end of the channel splitting the collective stream into another set of substreams so as to permit separate recovery of one or more of the substreams at the outlet end of the channel, continuously removing all of the substreams flowing from the outlet ports at the outlet end of the channel, and during the separation process occuring in the channel subjecting the channel to a special transverse driving force or gradient described hereinafter having a component perpendicular to the flow plane within the channel.

As a special embodiment, the invention provides a process for separation of particles using two or more of the above-noted channels in linked array or series wherein the channels are joined by fluid streams in which one or more of the outlet substreams from 1 channel or cell is fed to 1 or more of the inlet substreams of another cell or of more than one other cell.

The invention further provides a new type of separation apparatus or cell for use in the above-noted process which comprises one or more special split flow thin separation cells which permits one to effect the above-noted rapid and efficient separation or fractionation of particles.

2. Prior Art

There is a growing need in industry for the separation of particles including both cell-size particles and those of submicron and macromolecular size, such as various viruses, latices and polymers. Various methods have been proposed, but in general, they have been too slow, too low in throughput, inefficient, expensive or have failed to effect the separation with the desired degree of resolution needed for commerical operations.

Some of the highest resolution techniques disclosed have been those based on field-flow fractionation as disclosed in U.S. Pat. Nos. 3,449,938, 4,147,621 and 4,250,026. Other references include Giddings, Anal. Chem. 57 945 (1983). and Giddings et al-Sep. Science and Tech. 18 (3) 293–306 (1983). These prior known methods, however, are limited in throughput as they are batch techniques that do not operate normally on a continuous basis. They are designed as analytical-scale techniques and they fail to resolve adequate quantities of material needed for many applications.

The prior known methods thus present a critical defect in meeting the needs of industry. The increasing competitiveness of industry and the rapid evolution of new technologies is now putting extraordinary demands on separation process. Many industrial processes require that many particulate and macromolecular materials be processed in a way that produces homogeneous fractions of narrow size distribution. Where separation processes are used to produce these materials, the processes must have a relatively high throughput so that the required amount of material can be processed. In addition, the operation is preferably made as simple as possible. Continuous separation processes are desirable both from the point of view of simplicity of operation and the ability to process large quantities of materials.

This demand for effective preparative methods are particularly stringent in a rapidly growing area of biotechnology. Here the resolution must be high in order to remove a plethora of unwanted (and in some cases hazardous) contaminants from the products, and yet the processes must be simple enough and provide adequate throughput for economic viability. In biotechnology there is one additional demand; the separative processes must often occur rapidly so that sensitive biological species are not long removed from their normal stable environments.

There is thus a rapidly growing need for new separation technology for which the througput is continuous, the resolution is high, and the separation is fast. In addition, because of the enormous variety of separation needs, the separation process should preferably be based on as large a variety of molecular and particulate properties as is possible.

The unexpected superior results obtained by the present process as compared to the prior known techniques, such as field flow fractionation, are shown in Example II. As shown therein even by using a smaller cell volume and lower concentrations of solids in the feed suspension, the present process achieves a rapid throughput some 1400 times greater than that achieved in the field-flow fractionation technique. In addition, the process gives excellent resolution, is fast and uses simple equipment, and clearly meets the needs of industry as noted above.

It is an object of the invention, therefore, to provide a new and efficient process for particle fractionation. It is a further object to provide a new process for separation of particles from fluid media which can be accomplished in a rapid and efficient manner. It is a further object to provide a new process for particle fractionation which permits high resolution of separation. It is a further object to provide a process for separation of particles from fluid media which can be operated in a continuous manner. It is a further object to provide a new process for particle fractionation which permits separation on a single pass through the apparatus. It is a further object to provide a new separation process for particles which is economical to operate and uses inexpensive equipment. It is a further object to provide a new type of separation channel or cell which can be operated singly or in combination with other cells. It is a further object to provide a new split flow thin separation cell which gives superior unexpected results in the separation of particles. These and other objects will be apparent from the following detailed description thereof.

SUMMARY OF THE INVENTION

It has now been discovered that these and other objects may be accomplished by the new process of the present invention which comprises a rapid and very efficient continuous process for separation of particles.

The new process of the invention broadly comprises continuously introducing two or more fluid substreams of different composition into the inlet ports of a thin enclosed channel having an inlet end and an outlet end and having a thickness which is very thin compared to the other two dimensions, and bringing the substreams into contact with adjacent substreams so as to collectively form a series of thin laminae flowing parallel to one another within the channel and in contact with one another over a sufficient length of channel to allow a desired level of mass transport between and through laminae without substantial hydrodynamic mixing between the laminae, continuously introducing the fluid medium containing the particles to be separated as one or more of the fluid substreams and, indepedently of the particle concentration, varying the fluid composition of the different substreams as needed to realize separation, at the outlet end of the channel maintaining at least one means for splitting the collective streams into another set of substreams so as to permit separate recovery of one or more of the substreams at the outlet end of the channel, continuously removing all of the substreams separated at the outlet ports at the outlet end of the channel, and during the separation process subjecting the channel to a special transverse driving force or gradient described herein having a component perpendicular to the direction of flow in the channel or cell.

It has been surprisingly found that this process solves many of the defects of the prior known techniques and presents for the first time a very efficient process for the preparative separation of particles and molecules. The process can be operated on a continuous basis while most prior known techniques have been limited to batch operations. The new process is very time efficient and effects the separation on a single pass through the channel or through a series of such channels, while prior known techniques are either much slower or they require many repeated operations to obtain the desired amount of product. This unexpected superiority of the present process is clearly shown in Example II at the end of the specification wherein even by using a smaller cell volume and lower concentration of solids in the feed suspension, the present process achieves a throughput some 1400 times greater than that achieved by a prior known method.

The above-noted superior results are clearly surprising because it was expected prior to this invention that the throughput of a separation system increased with the thickness of the channel or cell or column in which it was carried out, and if one used a very thin channel, the throughput would correspondingly be very small. It was found, however, that this limitation is bypassed when operating according to the present invention. Thus, by using the operating conditions of the present process, a great increase in the speed of separation can be realized using a thin channel while maintaining an unexpected high rate of throughput.

Further, the new process in part because of the thin channel and in part because of the way the substreams are brought together and their flow rate controlled, effects a very high degree of resolution for a continuous process, and is superior in this regard to many of the prior known techniques. An additional advantage of the new process is that it is effective not only for separating two different types of particles but can also be made effective in separating in a single continuous operation a number of different types of particles.

Further advantage is found in the fact that the process provides laminar flow, provides protection against convection, has excellent ability to sweep the walls clean and can be adjusted to almost eliminate unwanted particle accumulation in the system as characteristic of other prior known methods.

Furthermore, the new separation process is very rapid, gives high resolution and is very economical to operate using inexpensive equipment with low cost maintenance.

Particularly superior results in the separation of particles are obtained by an embodiment of the process of the invention wherein there are splitter means at the inlet end and at the outlet end. With one splitter means at each end, resolution can be significantly increased when the substreams are adjusted at the inlet end and the outlet such that the ratio of flow rates in the upper substream relative to the lower substream is greater at the outlet than at the inlet.

As used herein, the expression "upper" refers to the side of the channel into which the particle-containing substream is introduced, and the "lower" refers to the opposite side.

Superior results are also obtained by a further special embodiment involving a process for separation of particles linking two or more of the above-noted cells in series or in other arrangements wherein the cells are joined by fluid streams in which one or more of the outlet substreams from one channel or cell is fed to one or more of the inlet substreams of another channel or cell or of more than one cell as described in detailed hereinafter.

The new process of the invention is conducted in a newly designed and quite different apparatus broadly comprising a cell or channel system formed between two sets of opposing walls one set of which comprises an inlet end wall and outlet end wall, the thickness of the channel being very thin compared to the other dimensions, inlet port means for introducing fluid substreams near the inlet end of the cell or channel, at least one means at the outlet end of the channel for splitting the flow into substreams and permitting separate recovery of the substreams, means for removing the substreams at the outlet end, and means for effecting a transverse driving force or gradient a component of which is perpendicular to the direction of flow of the laminae in the channel and perpendicular to the planes of the laminae.

As special embodiments, the invention provides variations of the above-noted apparatus wherein there are one or more inlet port means and outlet port means at the ends or along the length of the channel, and one or more splitter means at both ends or along the length of the cell or channel.

As a further embodiment as to the apparatus, the invention provides one or more of the above-noted cells joined either in parallel or in series or other arrangment to effect the separation of a larger number of particle fractions from one another.

PATENTABLE DISTINCTIONS OVER THE PRIOR ART

The presently claimed split flow fractionation process is clearly patentable distinct from the old field flow fractionation process disclosed in U.S. Pat. No. 4,147,621. The present process, for example, is a continuous process, while the Giddings '621 process is limited to batch operation. The present process involves the introduction of two or more fluid substreams of different composition, while Giddings '621 has only one inlet means. The present process forms a series of thin laminae parallel to one another for sufficient length to allow mass transport without hydrodynamic mixing, while the Giddings '621 has no such special laminae. The present process has splitter means at the outlet end to split stream into at least two substreams to be collected separately, while Giddings '621 has no such splitter means at the outlet as the particles are collected in a stream along the flow axis. The present process has a plurality of at least two outlet means to recover separate substreams, while the Giddings '621 process is limited to only one outlet means. The present process involves the adjustment of flow ratio at both inlet and outlet ends, while such is not taught or suggested by Giddings '612.

The apparatus used in the present invention is further distinquished from the prior art in that it is very thin, e.g. less than 5 millimeters, and the channel has a very short length, e.g. no more than 20 centimeters. Such a small ribbon-like channel is clearly patentable distinct from the large trough like device shown in Poirier-U.S. Pat. No. 2,386,632.

DESCRIPTION OF THE DRAWINGS

The various objects and features of the present invention will be more fully understood by reference to the accompanying drawings.

DESCRIPTION OF THE PROCESS

Figure 5:
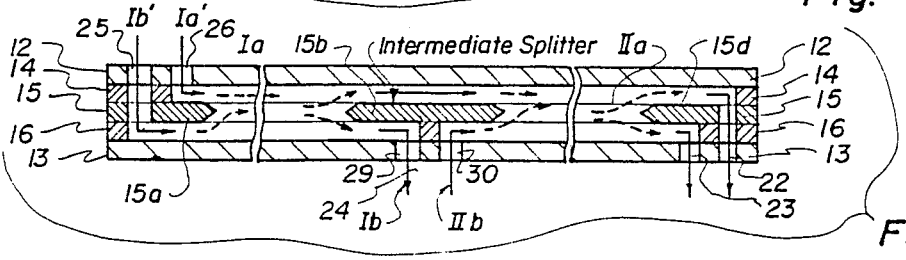
FIG. 5 is a side view of the thin channel illustrating the use of the physical splitter means at the inlet and outlet as well as the intermediate splitters in the interior.
Figure 6:
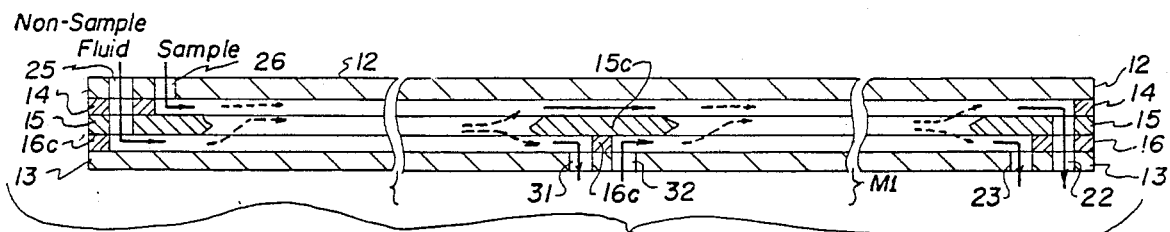
FIG. 6 is illustrates the presence of a series of m-1 physical splitter means within the interior of the channel.
Figure 7:
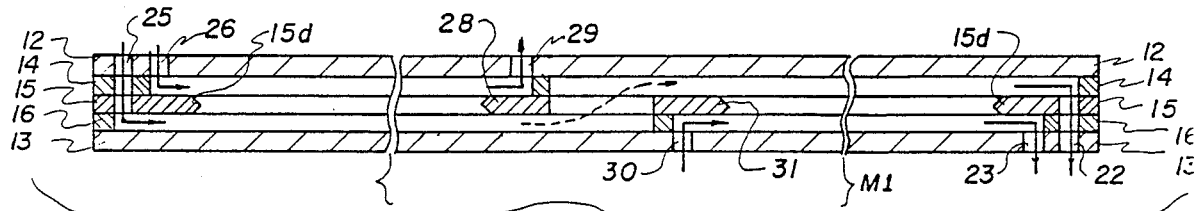
FIG. 7 is a side view of the thin channel illustrating a variation in the structure of the physical splitter means.

As used herein "channel" and "cell" are used to mean the same thing. They refer to a single relatively homogeneous separation unit with their own inlet and outlet port(s) and physical splitter mean(s). As shown in FIGS. 5, 6 and 7, several cells or channels can be contained in sequence in the same physical structure, or can be separate physical structures as in FIG. 5a.

Figure 1:
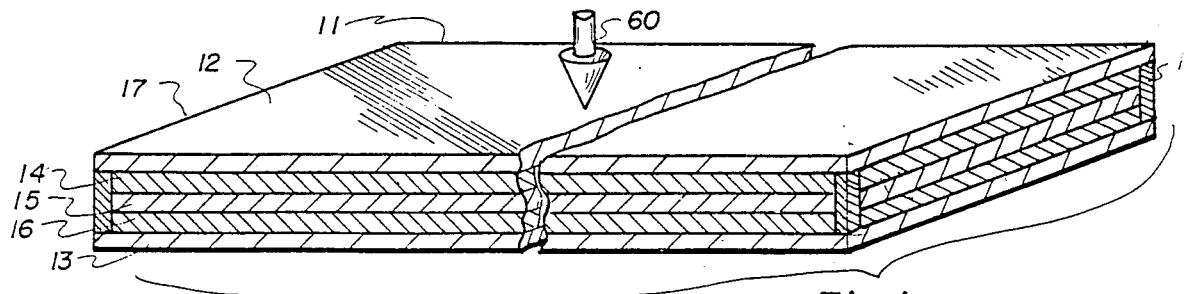
FIG. 1 is a perspective view of the thin elongated flow channel in this case constructed as a sandwich of individual layers of the type to be used in the process of the invention.

With reference to FIG. 1, the thin elongated channel or cell 11 comprises a top 12, bottom 13, inlet end 17 and outlet end 18, and spacer layers 14, 15 and 16 needed to create the desired channel volume. The presence of the transverse driving force or gradient is shown at 60 and is applied over the entire wall.

Figure 2:
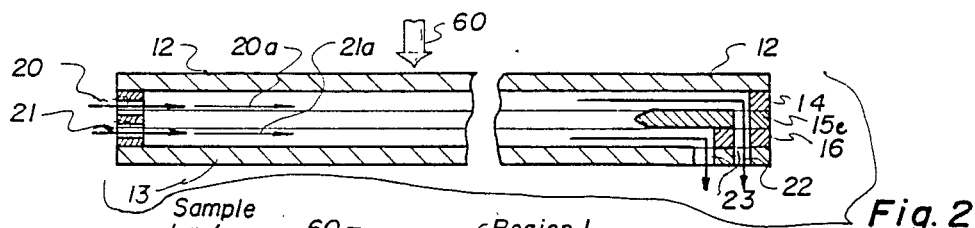
FIG. 2 is a side or edge view of the thin channel indicating in schematic form the placement of the inlet and outlet port means and the physical splitter means at the outlet end of the channel.

In the operation of the process, the fluid substream containing the particles to be separated is introduced at one of the inlet ports, e.g. 20 in FIG. 2, to form a lamina centered 20a, and a separate fluid substream introduced at inlet 21 to form a lamina centered at 21a. The particles are carried the length of the cell or channel where they are subjected more or less continuously to the field force 60 and undergo fractionation along the coordinate between walls 12 and 13. At the outlet end of the channel, the stream is split by splitter 15c to form the upper substream containing the low mobility particles which substream is removed at outlet 22, and form a lower substream containing the high mobility particles which substream is removed at the lower means 23.

It should be noted that while physical splitter means, such as 15c, are used to aid in the splitting of the substreams, the same effect can sometimes be obtained by using different outlet ports properly placed at the outlet end of the cell or channel. In a generic sense, splitter means as used herein refers to all such means, while "physical" splitter means refers to the actual physical separation means as shown by 15c.

Figure 3:
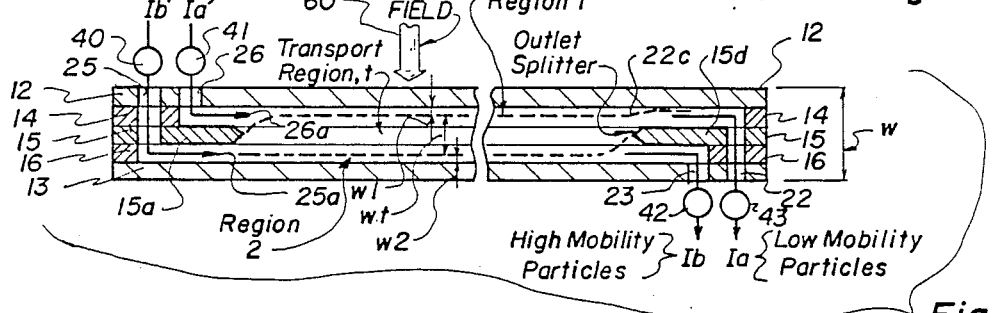
FIG. 3 is a side or edge view of the thin channel indicating in schematic form the placement of the inlet and outlet port means and physical splitter means at both the inlet and outlet ends of the channel and the approximate location of critical stream planes in the channel.

In the operation of the process using apparatus shown in FIG. 3, the fluid substream containing the particles to be separated is introduced at inlet means 26, and on striking physical splitter means 15a fans out into a thin laminar layer centered at 26a. A separate fluid substream is introduced at 25 and emerges from under physical splitter means 15a as another laminar layer centered at 25a. As the sample particles are carried the length of the channel, the transverse driving force or gradient 60 applied in a direction perpendicular to the flow axis and to the planes of the laminae effects the migration of the particles from the upper laminar layer, constituting region 1, called the imput region, towards region 2, called the collection region. If the applied force is gravitational or centrifugal, the larger (and or denser) particles will successfully realize this transfer, while the smaller particles will not, as this is the basis of the separation.

In the preferred operation of the apparatus as shown in FIG. 3, the substreams are adjusted by use of pumps 40, 41 at the inlet and flow controls 42 and 43 at the outlet. The adjustment is made such that the ratio of flow rates in the upper substream relative to the lower substream is greater at the outlet than at the inlet. This adjustment creates a cross-over flow, in which part of the fluid of the lower inlet substream 25a finds its way into the upper outlet substream 22c. This fluid transfer creates a critical buffer zone which is called the transport region, shown as region t in FIG. 3. With this region established by the unequal flow ratio, particles are not able to successfully reach region 2 and thus exit in the lower outlet substream 23 unless transport is completed across the thin transport zone. Without the unequal inlet/outlet splitting ratio, crossover flow and thus transport region t would disappear. In this case, particles entering at the bottom of input region 1 would easily and almost instantaneously transfer into the adjacent collection region 2 and thus exit from 23. Particles of the same kind entering at the top of region 1, however, would need a much greater time to reach region 2 because they would require transport the full distance across region 1. The signnificant difference in the time required for identical particles, entering at different positions within region 1, to transport into region 2 would lead to a loss of selectivity. The interposition of transport region t, by contrast, would establish more or less equal transport path across which all particles would need to pass in order to reach region 2 and exit 23.

The principle upon which transport region t is established in the channel is illustrated by the dashed boundary lines (actually, boundary planes) we call "splitting planes" between the labeled regions. These splitting planes coincide with very specific stream-planes of fluid flow. The upper splitting plane follows the streamlines dividing the laminae formed by the upper and lower inlet substreams. Thus, if the entering sample particles underwent no transport relative to the fluid but simply followed their respective flow lines, all the incoming particles would stay in region 1, remaining above the upper slitting plane.

The splitting planes may swerve up or down near the active edges of the channel splitters. These deflections are transient, resulting from the brief transition from one steady-state flow condition to another near the splitter edges. These transients will have little effect on separative transport. The principle separative transport occurs in the body of the cell, where the streamplanes maintain a stationary position which depends upon the ratio of flow rates in upper and lower substreams. Normally one would use a higher flow rate through entry means 25 than entry means 26 in order to force the upper splitting plane to curve upward to a stationary position closer to the top than to the bottom wall. This compresses the imput region, which provides the narrow initial sample zone required for satisfactory resolution.

The lowest splitting plane, by contrast divides the channel into two regions according to where the fluid elements exit rather than enter. Because of the unequal flow rate ratios noted above, a substantial fraction of the fluid introduced into the bottom inlet substream 25a will emerge in the upper outlet substream 22c. This layer of fluid occupies region t of the figure, between the two splitting planes. Any particle which is to reach region 2, and thus be carried out of exit 23, must traverse this layer, which therefore constitutes a critical transport region within the channel. By proper adjustment of flow rates, this transport region can be made considerably thicker than region 1, thus making the particle's starting position from within region 1 of little consequence. This strategy enhances the sharpness of the separation.

In well-designed channels, the boundary streamplanes should lie parallel to the axis of the channel throughout all of the channel except in the very narrow transient zone in the immediate vicinity of the splitting edges of inlet and outlet physical splitters. The transport region is thus well defined by these two parallel boundary planes, and the above transport processes should be well behaved, reproducible, and calculable.

Thus use of a thin channel in the above configuration has several advantages. First of all, the thickness $w_t$ of the transport region is scaled to the channel thickness w and is therefore smaller in thin channels. This leads to rapid transport across region t. Secondly, separative transport across the thin dimension of a thin channel, unlike a thicker channel, is relatively free of distortions. Thirdly, the thin channel configuration is a stabilizing influence against convection. Convection must be guarded against, especially in the case where a concentrated stream of dense sample particles is introduced into stream 2. However, additional stabilization against convection can be provided by adding to the carrier stream some unobstrusive solute (such as sucrose) that will increase the fluid density in the lower part (or other selected parts) of the flow channel.

Figure 4:
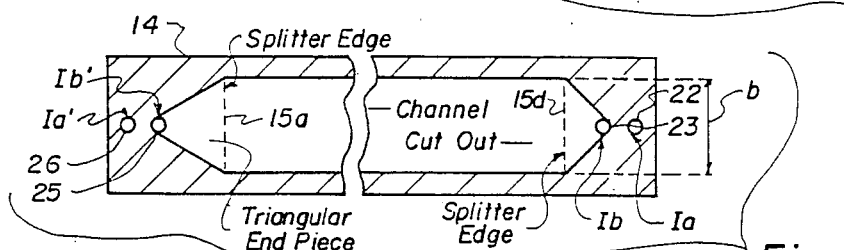
FIG. 4 is a top view of the thin channel indicating the cut-out used for the bottom spacer of the three spacers used to obtain the channel volume and the location of the physical splitter means at the inlet and outlet ends of the channel.

The one cell system described above, requiring binary inlet and outlet splitting, will normally be constructed with three thin films of spacer material, one film for each of the two entering and exiting flow conduits and another for the stream-splitting element between them. Other means, however, might be found for introducing thin splitting elements into the ends of the channel and in some case physical splitting means may not be required, the stream splitting being accomplished by the careful placement of outlet ports. The upper and lower split-flow conduits will normally converge to a point as shown in FIG. 4 for convenient introduction and withdrawal of the various substreams. As shown in FIG. 4, which is a top view of the channel, the point of introduction and outlet is normally located at the apex of the triangle-like end pieces.

Figure 10:
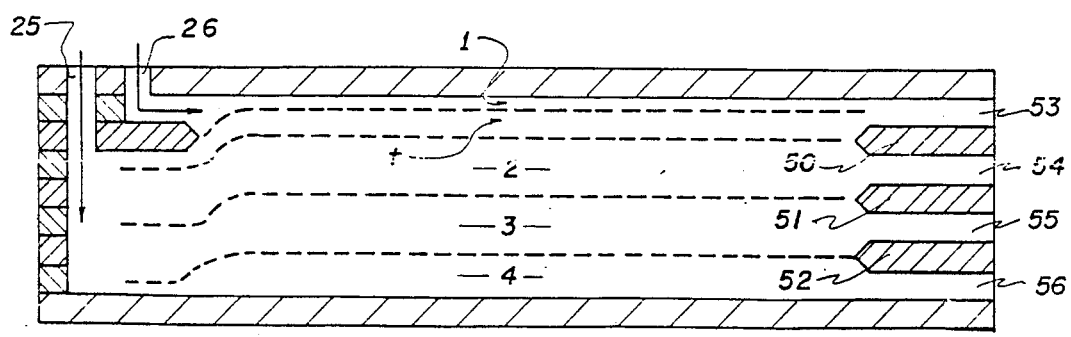
FIG. 10 is a side view of the channel showing the use of mutiple physical splitter means at the outlet end of the channel.

If desired, a larger number of fractions can be simultaneously and continuously collected by using a multi-split outlet. A channel with this type of outlet is illustrated in FIG. 10 showing the use of multiple splitters 50, 51 and 52 to form multiple outlets 53, 54, 55 and 56. Cross-over flow, with a resulting transport (t) zone, is used to advantage here as well as in the binary-split system. Cross-over flow, as before, reduces the thickness of the initial sample zone and thus improved resolution. Different outlet substreams are shown as (1, 2, 3 and 4). The trans port zone greatly sharpens the resolution between the particle populations collected in substreams 53 and 54. While the multi-split outlet system could be used without crossover flow, the resolving power would be reduced.

A channel with the outlet split into n outlet streams for the collection of n fractions would require 2n-1 spacer elements, as suggested by FIG. 10, thus spacer elements for 50, 51, 52, 53, 54, 55 and 56. A multi-split inlet with up to n flow elements can be simultaneously used to introduce density of pH gradients, if desired.

Such gradients can be used for quasi steady-state operation, yielding continuous and rapid separation based on the same underlying steady-state mechanism as used for isopycnic sedimentation and isoelectric focusing.

The dimensions of cells with multi-split outlets and-/or inlets might vary widely. However, it is important that the channel thickness w remain small for rapid mass transport and laminar flow; it is also essential that $w < < b$ (b=channel breadth) to avoid excessive edge effects which reduce resolution. Edge effects could be eliminated altogether by some form of sheath flow. An example of a channel with a relatively large w would be one with flow split into n=10 outlet streams, requiring $2n-1=19$ spacer layers. If each layer were 100 μm (approx. 0.004 in) thick, w would be 1.9 mm. This w would work best with a breadth b of 2 cm or preferably more to satisfy the condition $w < < b$. Length L would probably lie in the range 2–50 cm, but might be longer. Channels thinner than 1.9 mm could be made with thinner spacer layers (although flow-space and splitter uniformity would be harder to maintain) or with smaller n, or both. Binary-split cells (n=2) would tend to be thinner (e.g. $3 \times 100$ μm=300 μm) than mulit-split cells.

Figure 8:
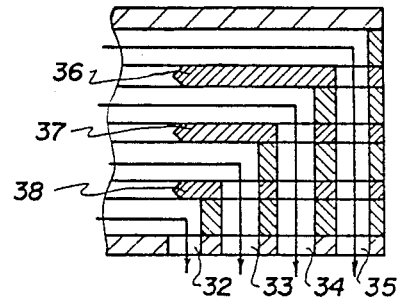
FIG. 8 is a side view of the outlet end of the channel illustrating the use of four outlet means.

A preferred system necessary to handle the various streams flowing out of (or into) a multi-split end is illustrated in FIG. 8 wherein the multiple splitters are shown as 36, 37 and 38 and the outlet ports shown as 32, 33, 34 and 35. Here the individual flow streams would exit (or enter) the channel via narrow conduits or slits passing through the other spacer layers and out one of the two walls. Normally, each stream would converge to the apex of a triangular end piece before exiting for convenience. Once outside the channel, each stream might flow through a segment of narrow tube or other flow restrictor for flow control. By varying the relative resistance of the restrictors, different fractions could be shifted up and down the array of exit ports to optimize fraction purity.

Figure 9:
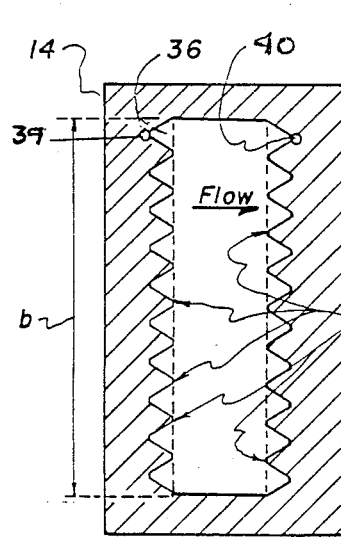
FIG. 9 is a top view of the thin channel illustrating the use of a series of inlet and outlet means as well as a series of physical splitter means.

The throughput of the different cells described above will be relatively high despite the small cell volumes because of the short transit times and the continuous operation. Throughput can be increased further by using banks of such channels working in parallel or by increasing channel breadth. Excessive channel breadth (for example, $b > L$), however, might lead to non uniform flow and thus nonconstant transit times because of disturbances originating in broad triangular end pieces. This problem can be remedied by using a series of triangular inlets and outlets, each of moderate breadth, for a single cell of considerable breadth, as illustrated in FIG. 9. In FIG. 9, the inlet means is illustrated by 39 and the outlet means by 40. The edge of the splitter means is illustrated by 36.

The single-channel systems described above can be expanded in another way to achieve the separation of multiple fractions instead of just two. Instead of using a multi-split outlet to a single cell, one can use a number of binary-split (or simply binary) separation cells or other related cell types to form a serial array of cells along the main flow axis. This is illustrated for 2 linked cells by FIG. 5. In this figure, the flow stream encounters an intermediate (rather than terminal) splitter 15b after the first binary separation cell. The intermediate splitter shunts the lower (high mobility) stream 1b out of the channel port 29 for collection but retains the upper (low mobility) stream 1a, simply transfering it through the splitter region to emerge as sample input stream IIa' for the second binary separation unit. This stream is then joined by a new fluid stream IIb' at input means 30 tc establish the conditions, including adequate cross over flow, necessary for another binary separation. The length of the second separation cell and the flow rates of carrier streams IIb' and to some extent IIa, can be adjusted to achieve separation around another critical value of mobility, different from that utilized to divide the particle population in the first flow cell. If the cutoff value $m_c$ of the generalized mobility (e.g. sedimentation coefficient in the case of a sedimentation field) in the second unit is adjusted to be slightly below that in the first, a narrow fraction of particles having mobilities between the two cutoff values will emerge in stream IIb. Streams 1b and IIa would contain the high-mobility and low mobility tails, respectively. With further adjustments, the original sample would be divided into different mobility ranges among the three outlet streams 1b, IIb and IIa.

Separations of higher order than ternary could be achieved by adding additional intermediate splitters as suggested by FIG. 6. In that figure m may be 2 or any no. greater than 2, and 31 illustrates the outlet means and 32 the inlet means for each of such additional units, and intermediate splitter 15c.

A system of linked cells with an alternate form of intermediate splitter is illustrated in FIG. 7. This figure shows the presence of intermediate splitter 28 with 29 the outlet port. 30 represents the new inlet port and 31 the new intermediate splitter.

Figure 5A:
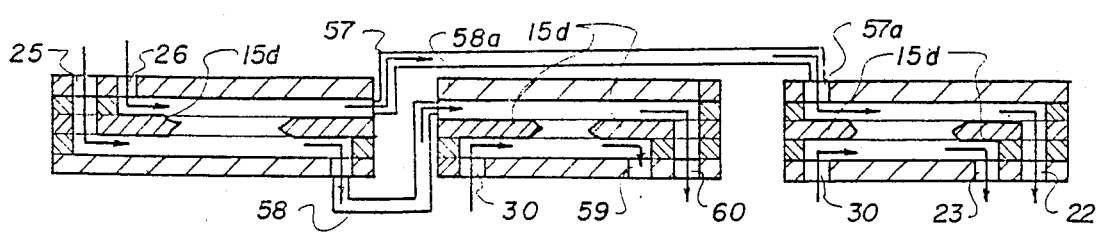
FIG. 5a shows separate cells linked together.

A system of linked cells each contained in a different structural unit is illustrated in FIG. 5a wherein 57 represents a conduit to carry the upper stream to a third cell unit at opening 57a, 58 is a conduit to carry the lower substream to the top of a second cell at opening 58a and 30 is the inlet port for a new substream. The upper substream of the second cell is removed at opening 60 and the lower substream of that cell is removed at port 59. In the third cell, the upper substream is removed at port 22 and the lower substream is removed at port 23.

The above examples barely begin to illustrate the numerous possibilities with linked-cell systems. Different separation cells can be distributed as desired over an extended 3 dimensional matrix. The matrix, by way of example, could be formed from a large number of thin spacer layers, each with sections cut-out in such a manner that the interconnected cells are formed in proper relationship to one another. Different substreams from one cell could, for example, be diverted sideways to different locations, each to enter its own cell or series of cells specially designed for processing that substream. Thus various sample containing streams and substreams could be divided, merged with other streams, recirculated, and/or introduced at different levels of either multi-split or binary-split cells. In short, the sample-containing streams could be directed through mazes of cells of arbitrary structure and complexity. This design freedom would be supported by the natural versatility of "plumbing" in thin-cell systems composed of multilayers of thin spacer material. Substreams could cross one another at different levels and they could pass through small aperatures in other layers to reach different lateral positions. In general, they could conduct fractions around rather freely over the 3 dimensional structure containing the various split cells.

It is possible to establish conditions such that different components will approach different steady-state distributions across the lateral coordinate. These distributions-or distributions approaching the steady state- can be converted into continuous separation using split-flow channels much as before. Again, the short lateral coordinate will greatly hasten the approach to steady-state, thus increasing fractionation speed and throughput.

DETAILS OF THE INVENTION

The type and size of the particles to be separated may vary over a wide range depending on flow conditions and the type and strength of field applied. The particles may be as small as polypeptides and as large as biological cells. Preferably, when gravity is the force field, the particles range in size from about 1 $\mu$m to 100 $\mu$m. The particles may also vary as to density and shape, and the conditions of the separation process will be adjusted accordingly.

The fluid in which the particles to be separated are contained may also vary over a wide range. In most cases, the fluid will be that in which the particles are normally prepared or contained, such as aqueous buffers for bioligical particles. In other cases, the particles are contained in specially prepared fluids or solutions in which the density, pH or other fluid characteristic is controlled in order to optimize the separation.

The fluid substream(s) introduced at the inlet end which do not contain the particles may also be varied or may contain modifiers (such as density modifiers) to increase the resolution and throughput. The fluid may be any liquid, aqueous or non-aqueous, and may be miscible or nonmiscible with the liquid in the particle-containing substream.

The concentration of the particles in the incoming particle-containing substream may also vary widely from extreme dilutions up to about 20% or more. In most cases, the concentration will vary from about 0.1% to about 5% by weight.

The special transverse driving forces or gradients used in the process of the invention are singly or in combination forces or gradients which effect transverse movement or effect transverse movement of particles at differentrates, oe effect movement to different transverse equilibrium or quasi-equilibrium positions. A component of each force or gradient utilized is applied perpendicular to the plane of the stream flow, i.e. along the transverse axis. The forces and gradients include, among others, sedimentation forces, such as caused by gravitation and centrifugation, electrical, dielectrical, cross flow, thermal gradients, density gradients, concentration gradients, and the like. Combination of one or more forces or gradients can be used as desired or needed. Preferred forces include sedimentation forces, such as caused by gravitation and centrifugation, and concentration and cross flow gradients. A particularly preferred field force includes the use of gravity where the channel is formed in a rectangular configuration as shown in FIG. 1 with the large sidewall surfaces oriented perpendicular to the gravitational force.

The strength of the force or gradient to be applied to the channel varies depending on several factors, such as particle mobility, thickness of separation cell, fluid density, diffusion coefficient, etc. and is best determined for each individual case. Generally, the highest practical field strength is preferred because throughput usually increases with field strength.

The temperature employed in the separation process may vary over a wide range, but generally will range between about 0° C. and 25° C.

The rate of introducing the above-noted substreams, some containing the particles and some not, may vary over a wide range. In general, the rate of introduction of the substreams will vary from about 0.1 ml/min. to about 100 ml/min.

As noted above, superior results are obtained when the rates of introducing the substreams at the inlet and the rates of withdrawal of the outlet streams are adjusted such that the ratio of flow rates in the upper substream relative to the lower substream(s) (as defined hereinabove) is greater at the outlet than at the inlet. This adjustment of the rate is conveniently accomplished by use of suitable pumping means.

The particle fractions obtained by the above-noted process will be recovered at the various outlet means in the form of fluid solutions or suspensions, which may be used directly as such or which may be subjected to further separation means, such as centrifugation or evaporation, to recover the particles themselves.

The apparatus to be used in the process of the invention may be constructed in a variety of ways with a variety of different materials and sizes as long as it provides the channel of the necessary thickness, the desired number of inlet and outlet means, the desired number of splitter means, pumping means, flow control means, and means for applying the desired transverse driving force or gradient.

The thickness of the channel is an important feature of the invention. The thickness of the channel along which dimension the separation takes place must be very thin compared to the other two dimensions, and preferably less than five millimeters. Particularly good results are obtained when the thickness varies from about 0.1 mm. to about 4 millimeters, and still more preferably from about 0.2 mm to about 2 mm.

The length and breadth of the channel may vary over a wide range as long as the thickness noted above is maintained. Increasing the length and breadth is desirable to increase throughput.

The channel should possess at least one inlet means for introducing the fluid substream containing the particles to be separated. Such means, which may be ports or holes with or without pump means, may be located at the top of the inlet end or at the end of the separation cell as desired for the creation of the necessary substreams.

The channel should also possess at least one inlet means for introducing particle-free substream(s). These means, which also may be ports or holes with or without pump means, may be located at the bottom of the inlet end or at the end of the separation cell as desired for the creation of the desired substream(s). As noted, these means may include pump means which may be controlled manually or automatically.

The channel may also possess at least one splitter means at the outlet end of the channel, and in some cases a plurality of such splitter means at the outlet end depending upon the intended operation of the channel. Preferably, such splitter means at the outlet end may vary from about 1 to 6.

For improved results, the channel may also possess at least one splitter means at the inlet end of the channel again depending upon the intended operation of the channel.

For further improved results, one may also locate splitter means at intermediate locations along the length of the channel as shown in FIGS. 5, 6 and 7. These splitter means may also vary from about 1 to 6 or more in number depending on the intended operation of the channel.

The splitter means, at the outlet, inlet and along the length of the channel may be of any desired shape and size as long as they accomplish the purpose of splitting the channel stream into physically distinct laminae.

As noted hereinabove, the generic expression "splitter means" refers to all such means, including specially placed outlet ports, physical barriers, and the like. The expression "physical" splitter as used herein refers to the actual physical barrier as shown by 15d in FIG. 1.

The preferred physical splitters are preferably prepared from very thin material, such as plastic or metal sheeting and extend preferably only a short distance into the cell, e.g. 1–5 cm. They preferably extend through the tapered or triangular end regions of the cell so as to facilitate a clean separation of laminae.

The channel may be constructed of various thin spacer layers of various materials from which regions are cut out to create the space for the movement of the substreams through the channel. As noted above, for the creation of n channel outlets for the collection of n fractions one would need 2n-1 spacer elements. Thus, for the creation of outlets for two substreams, one would need three spacer elements. These elements may be cut to different shapes and sizes as long as they provide a uniform channel and they effect the desired division of the channel end regions into the proper number of stream corridors. In most cases it is desirable to cut triangular shaped pieces from the ends of some of the spacers to permit a smooth transition from the channel flow to the narrow inlets and outlets at the apices of the triangles as shown in FIG. 4.

The channel top, bottom and end walls as well as the spacer elements and splitters may be constructed of any suitable material. In general, they are preferably prepared from thin plastic materials, such as mylar, teflon, polycarbonates, and the like, or from metals, such as stainless steel, etc. In the event cross flow is used as the force, the sides of the channels may be permeable or semipermeable material.

To illustrate the process of the invention, the following examples are given. However, it should be understood that the examples are only for illustration and do not limit the scope of the invention.

EXAMPLE I

A thin channel having the dimensions of 15 cm×2 cm×0.38 mm (thickness) was prepared by clamping glass plates over three 0.005 inch thick spacer elements (two of teflon and one of stainless steel) as shown generally in FIGS. 3 and 4. The inlets for the particle substream and the particle free substream were at the top and the bottom of the inlet end respectively and the outlets for the recovered fractions were at the top and bottom of the outlet end respectively.

A dilute aqueous suspension of 10 $\mu$m and 15 $\mu$m diameter polystyrene latex beads was introduced at the particle substream inlet at a rate of 0.28 ml/min. An aqueous stream was introduced at the other inlet opening at a rate of 0.75 ml/min. At the outlet end, the upper substream was withdrawn at 0.75 ml/min. and the lower substream at 0.28 ml/min.

The rate of introduction of the particle substream and the particle-free substream and the rates of withdrawal of substreams at the outlet end are thus adjusted such that the ratio of the flow rates in the upper substream relative to the lower substream is greater at the outlet than at the inlet.

The channel was exposed to a field force of one gravity and was oriented horizontally so that the gravitational force was perpendicular to the flow plane.

The recovered fractions recovered at the outlets were examined by microscopy which showed excellent resolution between the 10 $\mu$m and the 15 $\mu$m particles.

EXAMPLE II

This example illustrate the unexpected superior results obtained in comparison to the prior known separation techniques such as the field-flow fractionation process.

A comparison of the throughput of the presently claimed process and of a field flow fractionation system was made using the same perpendicular driving force of gravity and the same sample or feed material. The sample consisted of glass microspheres ranging from 1–5 $\mu$m in diameter purchased from Polysciences, Inc. The object of this test was to divide this material into two fractions, one containing spheres in the approximate diameter range 4–5 $\mu$m and the other containing 1–4 $\mu$m spheres. Both methods yielded the desired fractions but the presently claimed process was found to process a mass of microspheres 1400 times greater than the field flow fractionation system in the same period of time. In addition, the present process operated with a much shorter particle dwell time in the separation cell than the field flow process and it avoided the problems of sphere sticking to the channel walls and the repetitive interruption of operation for new injections as encountered with the field flow fractionation process.

The steric field flow channel had a length of 78.3 cm, a thickness of 254 $\mu$m, and a breadth of 2.0 cm. The void volume was 3.85 mL. The flowrate was optimized at 4.7 mL/min. A 5 $\mu$L sample of a 2% by weight suspension of glass microspheres was injected at the head of the channel. The last partices of this 0.1 mg sample were eluted at a time of 23.4 min. Run repetitively, this procedure yielded a throughput of 0.1 mg/0.39 hrs equal to 0.256 mg/hr.

The cell of the present process was smaller than the field flow fractionation cell. Its length was 15 cm, its breadth 3.0 cm, and its thickness 381 $\mu$m, giving a cell volume of 1.71 mL, less than half of the 3.85 mL volume of the field-flow channel. The concentration of the glass spheres in the aqueous feed solution was 1% by weight. The flowrate of the feed stream (a') was 0.40 mL/min and that of the carrier stream (b') was 1.8 mL/min. The product was collected after separation in the two individual outlet streams flowing at 1.8 mL/min (a) and 0.40 mL/min (b). By running continuously under these conditions, this procedure yielded 360 mg/hr. Thus, despite the smaller cell volume and the lower concentration of solids in the feed suspension, this unique form of continuous operation has made it possible to achieve a throughput some 1400 times greater than that achieved with the field flow channel.

I claim as my invention:

1. A continuous process for fractionating small particles as small as polypeptides and no larger than biological cells contained in a fluid stream comprising:

a. continuously introducing two or more fluid substreams of different composition into the inlet end of a thin enclosed channel having an inlet end possessing at least two inlet means and an outlet end possessing at least two outlet means and having a thickness which is very thin compared to the other two dimensions and is less than 5 millimeters, and has a length of not more than about 20 centimeters, and bringing a substream into contact with adjacent substreams so as to collectively form a series of thin laminae flowing parallel to one another within the channel and in contact with one another over a sufficient length of channel to allow a desired level of mass transport between and through the laminae without substantial hydrodynamic mixing between the laminae, b. continuously introducing a fluid medium containing the particles to be separated by means of one of said inlet means into one or more of the fluid substreams and varying the fluid composition of the non-particle containing substreams as needed to realize separation, c. at the outlet end of the channel splitting the collective channel stream into another set of substreams so as to permit separate recovery of at least two of the substreams at separate outlet means at the outlet end of the channel, d. adjusting the flow rates at the inlet end as well as at the outlet end so as to obtain the desired separation, e. continuously removing all of the substreams being separated at least two separate outlet means at the outlet end of the channel, f. during the separation process subjecting the channel to one or more transverse driving forces or gradients having a component perpendicular to the plane of the flow stream in the channel, and being selected from the group consisting of gravitation, centrifugation, electrical, dielectrical forces, cross-flow forces, temperature gradients, density gradients and concentration gradients, and combinations thereof.

2. A process as in claim 1 wherein the thickness of the channel varies from about 0.1 mm to 2.0 mm.

3. A process as in claim 1 wherein there are two or more of such separation cells or channels joined by fluid streams in which at least one of the outlet substreams from one cell is fed to at least one of the inlet substreams of another cell or of more than one cell.

4. A process as in claim 1 wherein means are employed at the inlet end of the channel to introduce two separate substreams.

5. A process as in claim 1 wherein splitter means are employed at the outlet end of the channel to split the stream into two substreams as it reaches the end of the channel.

6. A process as in claim 1 wherein the particles are introduced through the upper inlet substream and the flow rates of all substreams introduced at the inlet end as well as the flow rates of all of the substreams at the outlet end are varied such that the ratio of the flow rates in the upper substream relative to the lower substream or substreams is greater at the outlet end than at the inlet end and thereby creating a cross-over flow of the substreams.

7. A process as in claim 1 wherein the transverse driving force or gradient is centrifugation.

8. A process as in claim 1 wherein the transverse driving force or gradient is a temperature gradient.

9. A process as in claim 1 wherein the transverse driving force or gradient is a gradient in the fluid composition or in the concentration of a modifying material, established by introducing different compositions or different concentrations of said material into different inlet substreams.

10. A process as in claim 1 wherein the transverse driving force or gradient is a cross-flow.

11. A process as in claim 1 wherein the transverse driving force or gradient is a gradient in the concentration of sample particles, leading to separation based on different diffusion rates.

12. A process as in claim 1 wherein two transverse driving forces or gradients are combined.

13. A process as in claim 1 wherein the transverse driving force or gradient is a combination of gravitation and a density gradient.

14. A process as in claim 1 wherein the transverse driving force or gradient is a combination of centrifugation and a density gradient.

15. A process as in claim 1 wherein the transverse driving force or gradient is a combination of gravitation and cross flow.

16. An apparatus for separating small particles into desired fractions consisting of a separation cell or channel comprising:

a. a channel system formed between two sets of opposing walls, the end set of walls comprising an inlet end wall and an outlet end wall, and the thickness of the channel being very thin compared to the other two dimensions and being less than 5 millimeter and the length of the channel being not more about than 20 centimeters, b. an inlet means for introducing a fluid stream containing the particles to be separated at the inlet end of the channel so as to constitute a substream entering the channel, c. at least one other inlet means for introducing an additional substream having different composition at the inlet end of the channel, d. at least one means at the outlet end of the channel for splitting the substreams into at least two substreams and permitting separate recovery of the said substreams, e. means for removing the split substreams at the outlet means at the outlet end of the channel, f. and means for effecting one or more transverse driving forces or gradients having a component perpendicular to the plane of the flow stream in the channel.

17. An apparatus as in claim 16 wherein the thickness of the channel varies from about 0.1 mm to 2.0 mm.

18. An apparatus as in claim 16 wherein there are two or more such separation cells or channels joined by fluid streams in which one or more of the outlet substreams from one cell is fed to one or more of the inlet substreams of another cell or of more than one other cell.

19. An apparatus as in claim 16 wherein the inlet end walls and the outlet end walls within the interior of the channel converge to a point to form a narrow inlet and outlet port for the substreams.

20. An apparatus as in claim 16 wherein there is a physical splitter means present at the inlet end of the channel to split the incoming stream into substreams.

21. An apparatus as in claim 16 wherein there are from 1 to 9 physical splitter means at the outlet end of the channel to split the substreams as they approach the outlet end of the channel.

22. An apparatus as in claim 16 wherein means are present to vary the flow rates of the substreams at the inlet end as well as the flow rates of the substreams at the outlet end so as to effect a cross-over flow in the channel.

23. An apparatus as in claim 16 wherein the transverse driving force or gradient is gravitation.

24. An apparatus as in claim 16 wherein the transverse driving force or gradient is a temperature gradient.

25. An apparatus as in claim 16 wherein the transverse driving force or gradient is a gradient in the fluid composition or in the concentration of a modifying material, established by introducing different compositions or different concentrations of said material into different inlet substreams.

26. An apparatus as in claim 16 wherein the transverse driving force or gradient is a combination of at least two forces or gradients selected from the group consisting of gravitation, centrifugation, dielectrical forces, cross flow forces, temperature gradients, density gradients and concentration gradients.

27. An apparatus as in claim 16 wherein the transverse driving force or gradient is a transverse flow or cross flow induced by flow across permeable or semi-permeable channel walls.

28. An apparatus as in claim 16 wherein the channel is constructed as a sandwich of thin spacer elements from which the channel volume and any splitting elements are created by cutting the appropriate volume and shape out of each of said spacer elements.

29. An apparatus as in claim 28 wherein triangular shaped pieces have been removed from the ends of some of the spacers so as to permit a smooth transition from the channel flow to the inlets and outlets.

30. An apparatus as in claim 16 wherein the channel is rectangular in shape.

31. A continuous process for fractinating small particles as small as polypeptides and no larger than biological cells contained in a fluid stream comprising:
  a. continuously introducing two or more fluid substreams of different composition into the inlet end of a thin enclosed channel having an inlet end possessing at least two inlet means and an outlet end possessing at least two outlet means and having a thickness which is very thin compared to the other two dimensions and is less than 5 millimeter, and has a length of not more than about 20 centimeters, and bringing the substream into contact with adjacent substreams so as to collectively form a series of thin laminae flowing parallel to one another within the channel and in contact with one another over a sufficient length of channel to allow a desired level of mass transport between and through the laminae without substantial hydrodynamic mixing between the laminae,
  b. continuously introducing the fluid medium containing the particles to be separated by means of one of said inlet means into one or more of the fluid substreams and varying the fluid composition of the non-particle containing substreams as needed to realize separation,
  c. employing one or more means along the length of the channel to split the stream as it passes along the channel causing one or more of the obtained substreams to enter the following section of channel as a new substream for that section, causing other substreams to exit the channel for collection, discarding or to enter another separation channel, and to introduce new substream into the channel from outside the channel,
  d. at the outlet end of the channel splitting the collective channel stream into another set of substreams so as to permit separate recovery of at least two of the substreams at separate outlet means at the outlet end of the channel,
  e. adjusting the flow rates at the inlet end as well as at the outlet end so as to obtain the desired separation,
  f. continuously removing all of the substreams being separated at at least two separate outlet means at the outlet end of the channel,
  g. during the separation process subjecting the channel to one or more transverse driving forces or gradients having a component perpendicular to the plane of the flow stream in the channel, and being selected from the group consisting of gravitation, centrifugation, electrical, dielectrical forces, cross-flow forces, temperature gradients, density gradients and concentration gradients, and combinations thereof.

32. An apparatus for separating small particles into desired fractions consisting of a separation cell or channel comprising:
  a. a channel system formed between two sets of opposing walls, the end set of walls comprising an inlet end wall and an outlet end wall, and the thickness of the channel being very thin compared to the other two dimensions and being less than 5 millimeter and the length of the channel being not more than 20 centimeters,
  b. an inlet means for introducing a fluid stream containing the particles to be separated at the inlet end of the channel so as to constitute a substream entering the channel,
  c. at least one other inlet means for introducing an additional substream having different composition at the inlet end of the channel,
  d. one or more means present along the length of the channel to split the stream as it passes along the channel causing one or more of the obtained substreams to enter the following section of channel as a new substream for that section, causing other substreams to exit the channel for collection, discarding or to enter another separation channel, and to introduce new substreams into the channel from outside the channel,
  e. at least one mean at the outlet end of the channel for splitting the substreams into at least two substreams and permitting separate recovery of the said substreams,
  f. means for removing the split substreams at the outlet means at the outlet end of the channel,
  g. and means for effecting one or more transverse driving forces or gradients having a component perpendicular to the plane of the flow stream in the channel.

* * * * *

UNITED STATES PATENT AND TRADEMARK OFFICE
CERTIFICATE OF CORRECTION

PATENT NO. : 4,894,146

DATED : Jan. 16, 1990

INVENTOR(S) : John C. Giddings

It is certified that error appears in the above-identified patent and that said Letters Patent is hereby corrected as shown below:

Column 1, line 8, the following should be inserted.

"Work on this invention was supported by funding from National Science Foundation contract 82158503".

Signed and Sealed this

Twenty-second Day of October, 1991

*Attest:*

HARRY F. MANBECK, JR.

*Attesting Officer*     *Commissioner of Patents and Trademarks*